United States Patent
Volk et al.

(10) Patent No.: US 7,910,591 B2
(45) Date of Patent: *Mar. 22, 2011

(54) PIPERAZINE DERIVATIVES OF ALKYL OXINDOLES

(75) Inventors: Balázs Volk, Budapest (HU); József Barkóczy, Budapest (HU); Gyula Simig, Budapest (HU); Tibor Mezei, Budapest (HU); Rita Kapillerné Dezsöfi, Budapest (HU); István Gacsályi, Budapest (HU); Katalin Pallagi, Budapest (HU); Gábor Gigler, Budapest (HU); György Lévay, Budakeszi (HU); Krisztina Móricz, Budapest (HU); Csilla Leveleki, Budapest (HU); Nóra Sziray, Budapest (HU); Gábor Szenasi, Uröm (HU); András Egyed, Budapest (HU); László Gábor Hársing, Budapest (HU)

(73) Assignee: EGIS Gyogyszergyar NYRT., Budapest (HU)

( * ) Notice: Subject to any disclaimer, the term of this patent is extended or adjusted under 35 U.S.C. 154(b) by 21 days.

This patent is subject to a terminal disclaimer.

(21) Appl. No.: 11/596,465

(22) PCT Filed: May 11, 2005

(86) PCT No.: PCT/HU2005/000050
§ 371 (c)(1),
(2), (4) Date: Oct. 1, 2007

(87) PCT Pub. No.: WO2005/108364
PCT Pub. Date: Nov. 17, 2005

(65) Prior Publication Data
US 2008/0161323 A1    Jul. 3, 2008

(30) Foreign Application Priority Data
May 11, 2004   (HU) .................................... 0400953

(51) Int. Cl.
*A61K 31/403*   (2006.01)
*C07D 209/34*   (2006.01)
*C07D 401/12*   (2006.01)
*C07D 405/12*   (2006.01)

(52) U.S. Cl. .............. 514/253.09; 514/254.09; 544/364; 544/373

(58) Field of Classification Search ........................ None
See application file for complete search history.

(56) References Cited

U.S. PATENT DOCUMENTS

| 4,452,808 A | 6/1984 | Gallagher, Jr. et al. |
| 5,010,079 A * | 4/1991 | Manoury et al. ......... 514/253.05 |

FOREIGN PATENT DOCUMENTS

| EP | 0 281 309 A | 9/1988 |
| EP | 0 354 094 A | 2/1990 |
| EP | 0 376 607 A | 7/1990 |
| WO | WO-98/08816 A1 | 3/1998 |

OTHER PUBLICATIONS

Volk et al. J.Med. Chem. vol.51(8), p. 2522-2532 (2008).*

* cited by examiner

*Primary Examiner* — Emily Bernhardt
(74) *Attorney, Agent, or Firm* — Birch, Stewart, Kolasch & Birch, LLP

(57) ABSTRACT

The present invention is concerned with new indol-2-one derivatives of Formula (I), which have favorable activity profile for the prophylaxis and treatment of disorders in the central nervous or in the cadiovascular system.

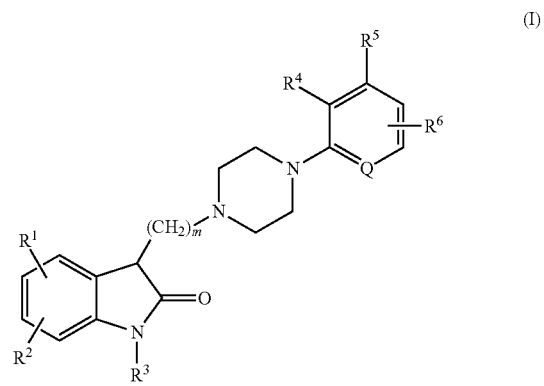

18 Claims, No Drawings

PIPERAZINE DERIVATIVES OF ALKYL OXINDOLES

TECHNICAL FIELD OF THE INVENTION

The invention relates to new, substituted indol-2-one derivatives and pharmaceutically acceptable acid addition salts thereof, furthermore to a process for the preparation of said compounds. The invention also encompasses pharmaceutical compositions containing said new indol-2-one derivatives and the use of said compounds for the treatment of diseases.

More particularly the present invention is concerned with new indol-2-one derivatives of the general Formula (I),

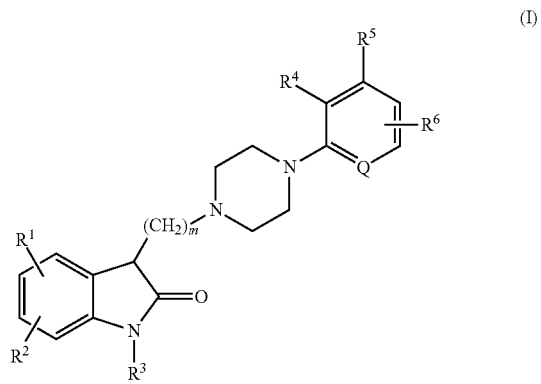

wherein
$R^1$ and $R^2$ independently represent hydrogen, halogen, alkyl or alkoxy having 1-7 carbon atom(s) or trifluoromethyl;
$R^3$ is hydrogen;
Q represents nitrogen, $R^4$ and $R^5$ independently represent hydrogen, halogen, trifluoromethyl, straight or branched chain alkyl or alkoxy having 1 to 7 carbon atom(s) and $R^6$ denotes hydrogen, halogen, alkyl or alkoxy having 1 to 7 carbon atom(s), or $R^4$ and $R^5$ together form ethylenedioxy; or Q is a CH group and $R^4$ and $R^5$ together form ethylenedioxy, and
$R^6$ stands for halogen or alkoxy having 1 to 7 carbon atom(s), or
Q is a CH group and $R^4$, $R^5$ and $R^6$ independently represent alkyl or alkoxy having 1 to 7 carbon atom(s) or halogen;
m is 1, 2, 3 or 4,
and pharmaceutically acceptable acid addition salts thereof.

TECHNICAL BACKGROUND OF THE INVENTION

U.S. Pat. No. 4,452,808 discloses 4-aminoalkyl indol-2-one derivatives having a selective $D_2$ receptor activity. These compounds can be used for the treatment of hypertension. One of the compounds provided by said patent, namely 4-[2-(di-N-propylamino)ethyl]-2(3H)-indolone, is used for the clinical treatment of Parkinson disease.

European patent No. 281,309 provides indol-2-one derivatives carrying an arylpiperazinyl-alkyl substituent in position 5, which can be applied for the treatment of psychotic conditions. One of the compounds described in said patent, namely 5-[2-[4-(1,2-benzisothiazol-3-yl)-1-piperazinyl]-ethyl]6-chloro-1,3-dihydro-2H-indol-2-one, exerts its activity by interaction with $D_2$, 5-$HT_{1A}$ and 5-$HT_2$ receptors and is used in the clinical treatment as an antipsychotic agent.

European patent No. 376,607 discloses indol-2-one derivatives substituted in position 3 by an alkylpiperazinyl-aryl group, which exert their activity on 5-$HT_{1A}$ receptor and are useful for the treatment of central nervous disorders.

In the international patent application WO 98/008816 indol-2-one derivatives containing a substituted alkyl-piperazinyl, substituted alkyl-piperidinyl or alkyl-cyclohexyl group in position 3 are disclosed. These compounds possess psychotrophic activity. Said patent specification is completely silent in mentioning anything about the activity profile of the said compounds, and as a field of application only the treatment of depression and anxiety are mentioned.

The acceleration of technical-social development in the twentieth century constitutes a permanent compulsion of adaptation for humans, which, in adverse cases, may lead to the occurrence of adaptation disorders. Adaptation disorders constitute an important risk factor in the development of diseases of mental or psycho-somatic origin, such as anxiolytic syndrome, stress disorder, depression, schizophrenia, disorders of the sense organs, gastrointestinal diseases, cardiovascular diseases and disorders of the secretory organs.

For the treatment of the above clinical patterns most widespreadly pharmaceuticals exerting their activity on the benzodiazepine system (e.g. diazepam) or on central 5-$HT_{1A}$ receptors (e.g. buspiron, ziprasidon) have been applied. In case of psychosomatic diseases anxiolytic therapy is often complemented by the administration of pharmaceuticals possessing antihypertensive (acting on $\alpha_1$ or $\alpha_2$ receptors), or antiulcerative ($H_1$-receptor antagonist) activity.

Anxiolytics of benzodiazepine type are accompanied, however, by several unpleasant side-effects. They have a strong sedative activity, cause decline of the power of concentration and memory and possess muscle relaxant effect. Said side-effects influence the quality of life of the patients in an adverse manner and thus restrict the scope of application of such pharmaceuticals.

Beside the stress occurring during adaptation to the environment another great problem of modern society is the rapid ageing of population. Owing to the results of modern medical science life expectancy has increased, and the diseases occurring due to ageing or developing in the declining years, particularly the number of mental diseases has grown in leaps and bounds. The solution of the treatment of Alzheimer's disease, vascular dementias and senile dementia has become a social problem.

As a result of the enumerated processes there is a strong need for new and efficient pharmaceuticals ensuring a more effective treatment of these diseases than those available for the time being.

SUMMARY OF THE INVENTION

The object of the present invention is to develop pharmaceutical ingredients having more favourable activity profile than those applied for the time being, which are devoid of the above-specified drawbacks and undesired side-effects and which, at the same time, can be used for the treatment and prophylaxis of disorders of the central nervous and cardiovascular system.

The invention is based on the surprising recognition that the substituted indol-2-one derivatives of the general Formula (I)—in contrast to the prior art compounds of similar structure—show a considerable binding to both 5-$HT_7$ and $\alpha_1$ receptors. Accordingly, it can be expected that their applicability will encompass the treatment of both central nervous and cardiovascular disorders.

DETAILED DESCRIPTION OF THE INVENTION

According to an aspect of the present invention there are provided novel 3-substituted indol-2-on derivatives of the general Formula (I), wherein
$R^1$ and $R^2$ independently represent hydrogen, halogen, alkyl or alkoxy having 1-7 carbon atom(s) or trifluoromethyl,
$R^3$ is hydrogen;
Q represents nitrogen,
$R^4$ and $R^5$ independently represent hydrogen, halogen, trifluoromethyl, straight or branched chain alkyl or alkoxy having 1 to 7 carbon atom(s),
$R^6$ denotes hydrogen, halogen, alkyl or alkoxy having 1 to 7 carbon atom(s), or
$R^4$ and $R^5$ together form ethylenedioxy; or
Q is a CH group and $R^4$ and $R^5$ together form ethylenedioxy, and $R^6$ stands for halogen or alkoxy having 1 to 7 carbon atom(s), or
Q is a CH group and $R^4$, $R^5$ and $R^6$ independently represent alkyl or alkoxy having 1 to 7 carbon atom(s) or halogen;
m is 1, 2, 3 or 4,
and pharmaceutically acceptable acid addition salts thereof.

The term "alkyl" used throughout this specification is intended to mean straight or branched chain saturated hydrocarbon groups having 1 to 7, preferably 1 to 4 carbon atom(s), (e.g. methyl, ethyl, 1-propyl, 2-propyl, n-butyl, isobutyl or tert. butyl group etc.)

The term "halogen" encompasses the fluorine, chlorine, bromine and iodine atoms and is preferably chlorine or bromine.

The leaving group can be an alkylsulfonyloxy or arylsulfonyloxy group, e.g. methylsulfonyloxy (mesyloxy) or p-toluenesulfonyloxy group; or a halogen atom, preferably bromine or chlorine.

The term "pharmaceutically acceptable acid addition salts" relates to non-toxic salts of the compounds of the general Formula (I) formed with pharmaceutically acceptable organic or inorganic acids. Inorganic acids suitable for salt formation are e.g. hydrogen chloride, hydrogen bromide, phosphoric, sulfuric or nitric acid. As organic acids formic, acetic, propionic, maleic, fumaric, succinic, lactic, malic, tartaric, citric, ascorbic, malonic, oxalic, mandelic, glycolic, phtalic, benzenesulfonic, p-toluenesulfonic, naphthalic or methanesulfonic acids can be used. Furthermore, carbonates and hydrocarbonates are also considered as pharmaceutically acceptable salts.

To a preferable group of the compounds of the general Formula (I) belong the compounds wherein Q is nitrogen;
$R^1$ and $R^2$ independently represent hydrogen, halogen, alkyl or alkoxy having 1 to 7 carbon atom(s) or trifluoromethyl;
$R^3$ is hydrogen;
$R^4$ and $R^5$ independently represent hydrogen, halogen, trifluoromethyl or straight or branched chain alkyl or alkoxy having 1 to 7 carbon atom(s),
$R^6$ is hydrogen, halogen, alkyl or alkoxy having 1 to 7 carbon atom(s), or
$R^4$ and $R^5$ together form ethylenedioxy;
m is 1, 2, 3 or 4;
and pharmaceutically acceptable acid addition salts thereof.

To another preferable group of the compounds of the general formula (I) belong the compounds wherein
$R^1$ and $R^2$ independently represent hydrogen, halogen, alkyl or alkoxy having 1 to 7 carbon atom(s) or trifluoromethyl,
$R^3$ is hydrogen;
Q is a CH group and $R^4$ and $R^5$ together form ethylenedioxy, $R^6$ denotes halogen or alkoxy having 1 to 7 carbon atom(s), or Q is a CH group and $R^4$, $R^5$ and $R^6$ independently represent halogen or alkyl or alkoxy having 1 to 7 carbon atom(s),
m is 1, 2, 3 or 4;
and pharmaceutically acceptable acid addition salts thereof.

Particularly preferable representatives of the compounds of general Formula (I) are the following derivatives:

3-{4-[4-7-chloro-2,3-dihydrobenzo[1,4]dioxin-5-yl)-piperazine-1-yl]-butyl}-5-fluoro-1,3-dihydro-2H-indol-2-one, 3-{4-[4-5-chloro-2-methoxyphenyl)-piperazine-1-yl]-butyl}-1,3-dihydro-2H-indol-2-one, 5-fluoro-3-{4-[4-(3-methoxyphenyl)-piperazine-1-yl]-butyl}-1,3-dihydro-2H-indol-2-one, and pharmaceutically acceptable acid addition salts thereof.

According to a further aspect of the present invention there is provided a process for the preparation of the compounds of the general Formula (I) and pharmaceutically acceptable acid addition salts thereof, which comprises a./reacting a compound of the general Formula (II),

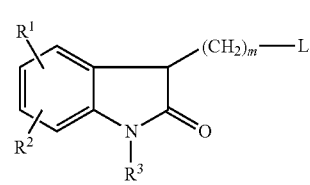

(II)

wherein L is hydroxy, with an arylsulfonyl chloride or a straight or branched chain alkylsulfonyl chloride having 1 to 7 carbon atom(s), preferably methylsulfonyl chloride, in the presence of an organic base, and reacting the thus-obtained compound of the general Formula (II), wherein L is aryl- or alkylsulfonyloxy, with a piperazine derivative of the general Formula (III)

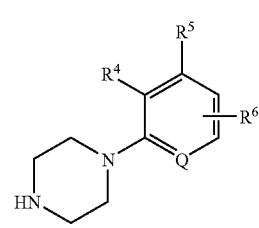

(III)

in the presence of an acid binding agent, or b./reacting a compound of the general Formula (V),

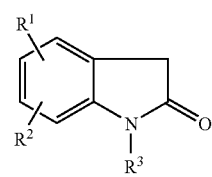

(V)

wherein $R^1$, $R^2$, $R^3$ are as stated above, with a compound of the general Formula (VI),

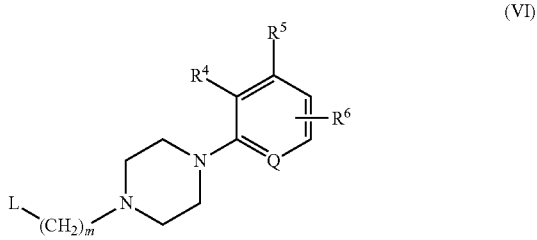

(VI)

wherein $R^4$, $R^5$, $R^6$ is as defined above, m is 1, 2, 3 or 4, L is a leaving group, preferably chlorine or bromine, in the presence of a strong base.

The compounds of the general Formula (I), wherein $R^1$-$R^6$, m and Q are as stated above, can be prepared by reacting a compound of the general Formula (II), wherein $R^1$-$R^3$ and m are as stated above, L is a leaving group, preferably alkylsulfonyloxy, most preferably methylsulfonyloxy, with a compound of the general Formula (III), wherein $R^4$-$R^6$ and Q are as stated above, according to methods known from the literature [Houben-Weyl: Methoden der organischen Chemie, Georg Thieme Verlag, Stuttgart, 1992, 4$^{th}$ Edition, vol. E16d (ed.: D. Klamann); R. C. Larock: Comprehensive Organic Transformations, 2. kiadás, John Wiley & Sons, New York, 1999, 789; D. A. Walsh, Y-H. Chen, J. B. Green, J. C. Nolan, J. M. Yanni *J. Med. Chem.* 1990, 33; 1823-1827].

During the preparation of the compounds of the general Formula (II) the formation of the substituents can be carried out in optional succession according to methods known from the literature. It is expedient to prepare the compounds of the general Formula (II) by reacting a compound of the general Formula (IV),

L-(CH$_2$)$_m$-L'  (IV)

wherein L and n are as stated above and L' is a leaving group or a group that can be converted into a leaving group, with a compound of the general Formula (V), wherein $R^1$-$R^4$ are as stated above, which has been prepared according to methods known from the literature Houben-Weyl: Methoden der organischen Chemie, Georg Thieme Verlag, Stuttgart, 1977, 4$^{th}$ Edition, vol. V/2b; A. R. Katritzky, Ch. W. Rees: Comprehensive Heterocyclic Chemistry, 1$^{th}$ Edition, Pergamon, Oxford, 1984, vol. 4. (ed.: C. W. Bird, G. W. H. Cheeseman), 98-150 and 339-366; G. M. Karp *Org. Prep. Proc. Int.* 1993, 25, 481-513; B. Volk, T. Mezei, Gy. Simig *Synthesis* 2002, 595-597].

The compounds of the general Formula (I), wherein $R^1$-$R^6$ and m are as stated above, can also be prepared by reacting a compound of the general Formula (V), wherein $R^1$-$R^3$ are as stated above, with a compound of the general Formula (VI), wherein $R^4$-$R^6$, m and Q are as stated above and L is a leaving group, by methods known from the literature [R. J. Sundberg: The chemistry of indoles, Academic Press, New York, 1970, vol. VII.; A. R. Katritzky, Ch. W. Rees: Comprehensive Heterocyclic Chemistry, 1$^{th}$ Edition, Pergamon, Oxford, 1984, vol. 4. (ed.: C. W. Bird, G. W. H. Cheeseman), 98-150 and 339-366; G. M. Karp *Org. Prep. Proc. Int.* 1993, 25, 481-513; A. S. Kende, J. C. Hodges *Synth. Commun.* 1982, 12, 1-10; W. W. Wilkerson, A. A. Kergaye, S. W. Tam *J. Med. Chem.* 1993, 36, 2899-2907].

The compounds of the general Formula (I), wherein $R^1$-$R^6$, m and Q are as stated above, can also be prepared by carrying out the formation of the substituents $R^1$-$R^6$ in different succession in the last reaction step. In this case a compound of the general Formula (I) is used as starting substance wherein all substituents are as stated above except the one to be formed, which can be any one selected from $R^1$, $R^2$, $R^3$, $R^4$, $R^5$ and $R^6$. The introduction and conversion of the substituents are carried out according to methods known from the literature [Houben-Weyl: Methoden der organischen Chemie, Georg Thieme Verlag, Stuttgart, 1977, 4$^{th}$ Edition, IV/1a-d; V/2b kötet]. During the introduction of the substituents application or elimination of protecting groups may become necessary. Such methods are specified in T. W. Greene, Protective groups in organic synthesis, John Wiley & Sons, 1981.

The compounds of the general Formulae (III), (IV), (V) and (VI) are known from the literature or can be produced by analogous methods.

The compounds of the general Formula (I) can be set free from their salts or converted into pharmaceutically acceptable acid addition salts according to methods known from the literature.

According to a further aspect of the present invention there are provided pharmaceutical compositions comprising as active ingredient a compound of the general Formula (I) or a pharmaceutically acceptable acid addition salt thereof in admixture with one or more conventional carrier(s) or auxiliary agent(s).

The pharmaceutical compositions according to the present invention contain generally 0.1-95% by weight, preferably 1-50% by weight, particularly 5-30% by weight of the active ingredient.

The pharmaceutical compositions of the present invention may be suitable for oral (e.g. powders, tablets, coated tablets, capsules, microcapsules, pills, solutions, suspensions or emulsions), parenteral (e.g. injection solutions for intravenous, intramuscular, subcutaneous or intraperitoneal use), rectal (e.g. suppositories) transdermal (e.g. plasters) or local (e.g. ointments or plasters) administration or for the application in form of implants. The solid, soft or liquid pharmaceutical compositions according to the invention may be produced by methods conventionally applied in the pharmaceutical industry.

The solid pharmaceutical compositions for oral administration containing the compounds of the general Formula (I) or pharmaceutically acceptable acid addition salts thereof may comprise fillers or carriers (such as lactose, glucose, starch, calcium phosphate, microcrystalline cellulose), binding agents (such as gelatine, sorbite, polyvinyl pyrrolidone), disintegrants (such as croscarmelose, Na-carboxymethyl cellulose, crospovidone), tabletting auxiliary agents (such as magnesium stearate, talc, polyethylene glycol, silicic acid, silicon dioxide) and surface-active agents (e.g. sodium lauryl sulfate).

The liquid compositions suitable for oral administration can be solutions, suspensions or emulsions. Such compositions may contain suspending agents (e.g. gelatine, carboxymethyl cellulose), emulsifiers (e.g. sorbitane monooleate, solvents (e.g. water, oils, glycerol, propylene glycol, ethanol), buffering agents (e.g. acetate, phosphate, citrate buffers) and preservatives (e.g. methyl-4-hydroxybenzoate).

Liquid pharmaceutical compositions suitable for parenteral administration are generally sterile isotonic solutions optionally containing, in addition to the solvent, buffering agents and preservatives.

Soft pharmaceutical compositions containing as active ingredient a compound of the general Formula (I) or a pharmaceutically acceptable acid addition salt thereof, such as suppositories, contain the active ingredient evenly dispersed in the basic material of the suppository (e.g. in polyethylene glycol or cocoa butter).

According to a further aspect of the present invention there is provided the use of 3-substituted indol-2-one derivatives of the general Formula (I) or a pharmaceutically acceptable acid addition salt thereof for the preparation of pharmaceutical compositions suitable for the treatment or prophylaxis of central nervous disorders or psychosomatic diseases, particularly generalized anxiety disorders, panic disease, compulsive disorder, social phobia, agoraphobia, phobias in connection with specific situations, post-traumatic stress disorders, post-traumatic memory disturbances, cognitive disorders, sexual dysfunction of central nervous system origin, depression, schizophrenia; gastrointestinal diseases and cardiovascular diseases.

The pharmaceutical compositions according to the present invention can be prepared by known methods of the pharmaceutical industry. The active ingredient is admixed with pharmaceutically acceptable solid or liquid carriers and/or auxiliary agents and the mixture is brought to galenic form. The carriers and auxiliary agents together with the methods which can be used in the pharmaceutical industry are disclosed in the literature (Remington's Pharmaceutical Sciences, Edition 18, Mark Publishing Co., Easton, USA, 1990).

The pharmaceutical compositions according to the present invention contain generally a dosage unit. The daily dosage for human adults can be generally 0.1-1000 mg/kg body weight of a compound of the general Formula (I) or a pharmaceutically acceptable acid addition salts thereof. Said daily dose can be administered in one or more portion(s). The actual daily dose depends on several factors and is determined by the physician.

According to a further aspect of the present invention there is provided the use of the compounds of the general Formula (I) or pharmaceutically acceptable acid addition salts thereof for the treatment or prophylaxis of disorders of the central nervous system and psychosomatic disorders including anxiety syndrome, particularly generalized anxiety disorders, panic disease, compulsive disorder, social phobia, agoraphobia, phobias in connection with specific situations, stress disorders, post-traumatic stress disorders, post-traumatic memory disturbances, cognitive disorders, sexual dysfunction of central nervous system origin, depression, schizophrenia, neurodegeneration followed by mental decline, Alzheimer's disease, stroke, dementias, furthermore gastrointestinal diseases and cardiovascular diseases, particularly hypertension.

The invention is based on the surprising recognition that the 3-alkyl-indol-2-one derivatives of the general Formula (I)—in contrast to the prior art compounds of similar structure—show a considerable binding to both 5-$HT_7$, and $\alpha_1$ receptors.

For the determination of 5-$HT_7$ receptor affinity human cloned receptors were used. The $\alpha_1$ receptor affinities were determined from isolated frontal cortex preparation of male Wistar rats weighing 120-200 g. The protein contents of membrane preparations were determined by the method of Lowry (1951).

In the course of 5-$HT_7$ and $\alpha_1$ receptor binding studies the ligands were $^3$H-lizergic acid diethylamide (LSD) (1.0 nM) and $^3$H-prazosine (0.3 nM). Clozapine (25 µM) and prazosine (1 µM) were used for the measurement of non-specific bindings. The $\alpha_1$ receptor binding studies were carried out according to the methods of Reader, and Greengrass (Reader, T. A., Briere, R., Grondin, L.: J. Neural Transm. 68, p. 79 (1987); Greengrass, P., Brenner, R.: Eur. J. Pharmacol. 55, p. 323 (1979)).

$IC_{50}$ is the concentration where the difference between the whole binding and non-specific binding is 50%. The compounds with an $IC_{50}$ value smaller than 100 nmol were considered effective in this test. The results of the experiments are presented in Tables 2 and 3.

TABLE 1

5-$HT_7$ receptor binding

| No. of Example | $IC_{50}$ nmole |
|---|---|
| 5. | <100 |
| 6. | <100 |
| 8. | <100 |
| 9. | <100 |
| 10. | <100 |
| 11. | <100 |
| 12. | <100 |

TABLE 2

$\alpha_1$ receptor binding

| No. of Example | $IC_{50}$ nmole |
|---|---|
| 5. | <100 |
| 6. | <100 |
| 8. | <100 |
| 9. | <50 |
| 10. | <50 |
| 11. | <50 |
| 12. | <100 |

As it can be seen from the data shown in Tables 1 and 2, the compounds according to the invention considerably bind to the 5-$HT_7$ and $\alpha_1$ receptors.

On the basis of the above experiments it can be established that the compounds according to the invention possess a valuable therapeutic profile rendering them suitable for the treatment or prophylaxis of mental and cardiovascular diseases, especially those specified above.

Further details of the present invention are provided in the following examples without limiting the scope of protection to said examples.

Preparation of Mesyl Esters (Process "A")

The appropriate 3-(4-hydroxybutyl)-oxindoles are prepared according to a method known from the literature [B. Volk, T. Mezei, Gy. Simig *Synthesis* 2002, 595; B. Volk, Gy. Simig *Eur. J. Org. Chem.* 2003, 18, 3991-3996].

55 mmoles of 3-(4-hydroxybutyl)-oxindole are dissolved in 150 ml of THF, 15.2 ml (110 mmoles) of triethyl amine are added to it, and the solution is cooled in an acetone-dry ice bath to −78° C. While stirring at the same temperature 8.5 ml (110 mmoles) of mesyl chloride are added dropwise to it and the solution is allowed to warm to room temperature. It is stirred at room temperature for 1 hour, the triethyl amine hydrochloride is filtered off, the filtrate is evaporated, the residue is taken up in ethyl acetate and extracted several times with 10% by volume hydrogen chloride solution until the pH of the aqueous phase has become acidic. The organic phase is dried over sodium sulfate, evaporated, the residual oil is crystallized by rubbing it with diisopropyl ether, stirred in 100 ml of diisopropyl ether, filtered, washed with hexane and dried. The product is purified by recrystallization from the solvent indicated after the melting point of the given substance.

Example 1

3-4-Mesyloxybutyl)-1,3-dihydro-2H-indol-2-one

The title compound is prepared according to process A starting from 3-(4-hydroxybutyl)-1,3-dihydro-2H-indol-2-one.

M.p.: 84-85° C. (heptane-ethyl acetate).
IR (KBr): 3180, 1705 (C=O) cm$^{-1}$.
$^1$H-NMR (CDCl$_3$, TMS, 400 MHz): 9.33 (1H, s), 7.22 (1H, d, J=7.1 Hz), 7.21 (H, t, J=7.0 Hz), 7.03 (1H, t, J=7.5 Hz), 6.93 (1H, d, J=7.6 Hz), 4.19 (2H, t, J=6.5 Hz), 3.49 (1H, t, J=6.0 Hz), 2.97 (3H, s), 2.05-1.98 (2H, m), 1.82-1.72 (2H, m) 1.58-1.40 (2H, m) ppm.
$^{13}$C-NMR (CDCl$_3$, TMS, 101 MHz): 180.5, 141.6, 129.1, 127.9, 123.9, 122.3, 109.9, 69.5, 45.7, 37.2, 29.6, 28.9, 21.6 ppm.

Example 2

5-Fluoro-3-(4-mesyloxybutyl)-1,3-dihydro-2H-indol-2-one

The title compound is prepared according to process A starting from 5-fluoro-3-(4-hydroxybutyl)-1,3-dihydro-2H-indol-2-one.

M.p.: 106-108° C. (hexane-ethyl acetate).
IR (KBr): 3169, 1702(C=O), 1356, 1175 (SO$_2$) cm$^{-1}$.
$^1$H-NMR (CDCl$_3$, TMS, 500 MHz): 1.43-1.55 (2H, m), 1.73-1.83 (2H, m), 1.97-2.05 (2H, m), 2.99 (3H, s), 3.50 (1H, t, J=5.9 Hz), 4.21 (2H, dq, J=1.4, 6.3 Hz), 6.86 (1H, dd, J=4.3, 8.4 Hz), 6.93 (1H, dt, J=2.3, 9.0 Hz), 6.97 (1H, dd, J=2.0, 7.3 Hz), 9.22 (1H, s) ppm.
$^{13}$C-NMR (CDCl$_3$, TMS, 125.6 MHz): 180.2, 158.9 (d, J=240.6 Hz), 137.5 (d, J=1.7 Hz), 130.8 (d, J=8.5 Hz), 114.3 (d, J=27.5 Hz), 111.9 (d, J=24.8 Hz), 110.4 (d, J=8.1 Hz), 69.4, 46.2, 37.3, 29.5, 28.9, 21.5 ppm.

Example 3

6-Fluoro-3-4-mesyloxybutyl)-1,3-dihydro-2H-indol-2-one

The title compound is prepared according to process A starting from 6-fluoro-3-(4-hydroxybutyl)-1,3-dihydro-2H-indol-2-one.

M.p.: 106-108° C. (hexane-ethyl acetate).
IR (KBr): 3161, 1705 (C=O), 1335, 1313, 1167 (SO$_2$) cm$^{-1}$.
$^1$H-NMR (CDCl$_3$, TMS, 500 MHz): 1.46-1.51 (2H, m), 1.78 (2H, kv, J=6.7 Hz), 2.00 (2H, q, J=8.1 Hz), 2.99 (3H, s), 3.46 (1H, t, J=5.9 Hz), 4.21 (2H, dt, J=1.5, 6.5 Hz), 6.68 (1H, dd, J=2.3, 8.8 Hz), 6.72 (1H, dt, J=2.3, 8.9 Hz), 7.15 (1H, dd, J=5.4, 8.1 Hz), 9.15 (1H, br s) ppm.
$^{13}$C-NMR (CDCl$_3$, TMS, 125.6 MHz): 21.6, 28.9, 29.7, 37.3, 45.3, 69.5, 98.6 (d, J=27.4 Hz), 108.7 (d, J=22.5 Hz), 124.5 (d, J=3.0 Hz), 124.9 (d, J=9.5 Hz), 142.8 (d, J=11.8 Hz), 162.6 (d, J=244.6 Hz), 180.7 ppm.

Example 4

5-Methyl-3-(4-mesyloxybutyl)-1,3-dihydro-2H-indol-2-one

The title compound is prepared according to process A starting from 3-(4-hydroxybutyl)-5-methyl-1,3-dihydro-2H-indol-2-one.

M.p.: 89-90° C. (hexane-ethyl acetate).
IR (KBr): 3175, 1710 (C=O), 1351, 1176 (SO$_2$) cm$^{-1}$.
$^1$H-NMR (CDCl$_3$, TMS, 400 MHz): 9.13 (1H, s), 7.03 (1H, s), 7.01 (1H, dd, J=7.9, 0.8 Hz), 6.81 (1H, d, J=7.9 Hz), 4.20 (2H, t, J=6.5 Hz), 3.45 (1H, t, J=5.9 Hz), 2.98 (3H, s), 2.33 (3H, s), 1.99 (2H, q, J=7.4 Hz), 1.79-1.75 (2H, m), 1.51-1.42 (2H, m) ppm.
$^{13}$C-NMR (CDCl$_3$, TMS, 101 MHz): 180.4, 139.1, 131.7, 129.2, 128.2, 124.7, 109.5, 69.6, 45.8, 37.2, 29.6, 28.9, 21.5, 21.0 ppm.

Coupling Reaction of Mesyl Esters with Bases (Process "B")

The melt of the secondary amine (12 mmoles) is warmed to 120° C. under slow stirring, and the mesyl compound (12 mmoles) and sodium carbonate (1.36 g; 12 mmoles) are added to it at the same temperature. The mixture is allowed to react for 1 hour, the melt is allowed to cool, ethyl acetate and water are added to it and the phases are separated. The organic phase is evaporated, the residual oil is subjected to chromatography on a short column using ethyl acetate as eluent. As main products the desired compounds are obtained.

Processing method 1: If the product purified by column chromatography gets crystalline upon rubbing with diethyl ether, it is filtered off and recrystallized from a mixture of hexane and ethyl acetate. The desired compounds are obtained in form of white crystals.

Processing method 2: If the basic product does not get crystalline upon the addition of diethyl ether, it is dissolved in 200 ml of ether, the slight amount of floating precipitate is filtered off and to the pure solution the calculated amount (1 molar equivalent) of hydrogen chloride dissolved in ether diluted with 50 ml of diethyl ether is dropped under vigorous stirring. The separated white salt is filtered off, washed with ether and hexane and dried in a vacuum pistol at room temperature for 3 hours.

Processing method 3: If the basic product does not get crystalline upon the addition of diethyl ether and does not provide a well-filterable salt with hydrogen chloride, it is dissolved in 100 ml of hot ethyl acetate, and a solution of 1 molar equivalent of oxalic acid dihydrate in 30 ml of hot ethyl acetate is dropped to it within 10 minutes, under stirring. The white oxalate salt gets separated upon cooling. It is filtered off at room temperature, washed with ethyl acetate and hexane and dried.

Example 5

3-[4-(4-Pyridin-2-yl-piperazine-1-yl)-butyl]-1,3-dihydro-2H-indol-2-one

The title compound is prepared according to process B by applying processing method 1 starting from 3-(4-mesyloxy-butyl)-1,3-dihydro-2H-indol-2-one and 1-(pyridin-2-yl)-piperazine.

M.p.: 131-132° C. (hexane-ethyl acetate).
IR (KBr): 3189, 1706 (C=O), 1665 cm$^{-1}$.
$^1$H-NMR (CDCl$_3$, TMS, 400 MHz): 1.59-1.38 (4H, m), 2.05-1.95 (2H, m), 2.35 (2H, t, J=7.5 Hz), 2.51 (4H, t, J=5.1 Hz), 3.47 (1H, t, J=5.9 Hz), 3.52 (4H, t, J=5.1 Hz), 6.61 (1H, t, J=6.1 Hz), 6.62 (1H, d, J=8.7 Hz), 6.89 (1H, d, J=7.7 Hz), 7.01 (1H, dt, J=1.0, 7.5 Hz), 7.20 (1H, t, J=7.8 Hz), 7.22 (1H, d, J=7.0 Hz), 7.45 (1H, dt, J=2.0, 7.9 Hz), 8.18 (1H, ddd, J=0.8, 2.0, 4.9 Hz) ppm.

$^{13}$C-NMR (CDCl$_3$, TMS, 101 MHz): 180.6, 159.5, 147.8, 141.7, 137.3, 129.7, 127.8, 124.0, 122.1, 113.2, 109.7, 107.0, 58.3, 52.9, 46.0, 45.1, 30.2, 26.7, 23.7 ppm.

Analysis for the formula C$_{21}$H$_{26}$N$_4$O (350.47): Calculated: C, 71.97; H 7.48; N, 15.99%. Found: C, 70.86; H 7.48; N, 15.76%.

Example 6

3-{4-[4-(7-Chloro-2,3-dihydrobenzo[1,4]dioxin-5-yl)-piperazine-1-yl]-butyl}-1,3-dihydro-2H-indol-2-one Monooxalate

The title compound is prepared according to process B by applying processing method 3 starting from 3-(4-mesyloxybutyl)-1,3-dihydro-2H-indol-2-one and 1-(7-chloro-2,3-dihydrobenzo-[1,4]dioxin-5-yl)-piperazine.

M.p.: 236-238° C.

IR (KBr): 3273, 3013, 1710 (C=O) cm$^{-1}$.

$^1$H-NMR (DMSO-d$_6$, TMS, 400 MHz): 1.38-1.22 (2H, m), 1.70-1.60 (2H, m), 1.95-1.75 (2H, m), 2.95 (2H, t, J=7.5 Hz), 3.18 (8H, br s), 3.44 (1H, t, J=6.1 Hz), 4.25 (4H, s), 6.64 (1H, d, J=2.4 Hz), 6.50 (1H, d, J=2.4 Hz), 6.84 (1H, d, J=7.7 Hz), 6.95 (1H, t, J=7.5 Hz), 7.17 (1H, t, J=7.6 Hz), 7.26 (1H, d, J=7.3 Hz), 8.7=2H, br s), 10.4 (1H, s) ppm.

$^{13}$C-NMR (DMSO-d$_6$, TMS, 101 MHz): 179.0, 164.7, 144.6, 142.9, 141.2, 135.1, 129.7, 127.8, 124.4, 124.2, 121.4, 111.4, 110.7, 109.4, 64.2, 64.1, 55.7, 51.2, 47.3, 45.1, 29.6, 23.7, 22.8 ppm.

Analysis for the formula C$_{26}$H$_{30}$ClN$_3$O$_7$ (532.00):

| Calculated: | C | 58.70 | H | 5.68 | Cl | 6.66 | N | 7.90%. |
|---|---|---|---|---|---|---|---|---|
| Found: | C | 58.67 | H | 5.77 | Cl | 6.67 | N | 7.85%. |

Example 7

5-Fluoro-3-[4-(4-pyridin-2-yl-piperazine-1-yl)-butyl]-1,3-dihydro-2H-indol-2-one

The title compound is prepared according to process B/1 starting from 5-fluoro-3-(4-mesyl-oxybutyl)-1,3-dihydro-2H-indol-2-one and 1-(pyridin-2-yl)-piperazine.

M.p.: 132-134° C. (hexane-ethyl acetate).

IR (KBr): 3180, 1705 (C=O) cm$^{-1}$.

$^1$H-NMR (CDCl$_3$, TMS, 400 MHz): 1.47-1.35 (2H, m), 1.59-1.52 (2H, m), 2.03-1.95 (2H, m), 2.36 (2H, t, J=7.6 Hz), 2.52 (4H, t, J=5.1 Hz), 3.48 (1H, t, J=5.9 Hz), 3.53 (4H, t, J=5.0 Hz), 6.64-6.59 (2H, m), 6.81 (1H, dd, J=4.3, 8.5 Hz), 6.91 (1H, dt, J=2.6, 9.2 Hz), 6.97 (1H, dd, J=2.0, 7.9 Hz), 7.47 (1H, dt, J=2.0, 7.1 Hz), 8.18 (1H, ddd, J=0.9, 2.0 Hz), 9.00 (1H, s) ppm.

$^{13}$C-NMR (CDCl$_3$, TMS, 101 MHz): 23.6, 26.7, 30.2, 45.1, 46.4, 53.0, 58.3, 107.0, 110.1 (d, J=8.0 Hz), 112.1 (d, J=24.4 Hz), 113.2, 114.1 (d, J=23.3 Hz), 131.3 (d, J=7.6 Hz), 137.4, 137.5, 147.9, 159.0 (d, J=239.9 Hz), 159.5, 180.2 ppm.

Analysis for the formula C$_{21}$H$_{25}$FN$_4$O (368.46):

| Calculated: | C | 68.46 | H | 6.84 | N | 15.21%. |
|---|---|---|---|---|---|---|
| Found: | C | 68.34 | H | 7.04 | N | 14.86%. |

Example 8

6-Fluoro-3-[4-(4-pyridin-2-yl-piperazine-1-yl)-butyl]-1,3-dihydro-2H-indol-2-one

The title compound is prepared according to process B by applying processing method 1 starting from 6-fluoro-3-(4-mesyloxybutyl)-1,3-dihydro-2H-indol-2-one and 1-(pyridin-2-yl)-piperazine.

M.p.: 136-137° C. (hexane-ethyl acetate).

IR (KBr): 3294, 1726 (C=O), 1689 cm$^{-1}$.

$^1$H-NMR (CDCl$_3$, TMS, 400 MHz): 1.43-1.38 (2H, m), 1.67 (2H, br s), 1.97 (2H, q, J=7.4 Hz), 2.55 (2H, br s), 2.74 (4H, br s), 3.42 (1H, t, J=5.9 Hz), 3.68 (4H, br s), 6.73-6.63 (4H, m), 7.13 (1H, dd, J=5.3, 8.2 Hz), 7.48 (1H, dt, J=2.0, 7.8 Hz), 8.20-8.17 (1H, m), 8.97 (1H, s) ppm.

$^{13}$C-NMR (CDCl$_3$, TMS, 101 MHz): 23.3, 25.6, 30.1, 44.3, 45.3, 52.5, 57.9, 98.4 (d, J=27.1 Hz), 107.2, 108.5 (d, J=22.1 Hz), 113.8, 124.7 (d, J=3.1 Hz), 124.9 (d, J=9.9 Hz), 137.6, 142.9 (d, J=12.2 Hz), 147.9, 159.0, 162.6 (d, J=244.5 Hz), 180.4 ppm.

Analysis for the formula C$_{21}$H$_{25}$FN$_4$O (368.46):

| Calculated: | C | 68.46 | H | 6.84 | N | 15.21%. |
|---|---|---|---|---|---|---|
| Found: | C | 68.14 | H | 6.83 | N | 15.03%. |

Example 9

3-{4-[4-(3-Methoxyphenyl)-piperazine-1-yl]-butyl}-1,3-dihydro-2H-indol-2-one Monooxalate

The title compound is prepared according to process B by applying processing method 3 starting from 3-(4-mesyloxybutyl)-1,3-dihydro-2H-indol-2-one and 1-(3-methoxyphenyl)piperazine.

M.p.: 208-211° C.

IR (KBr): 3160, 2579, 2456, 1707 (C=O) cm$^{-1}$.

$^1$H-NMR DMSO-d$_6$, TMS, 400 MHz): 1.36-1.24 (2H, m), 1.95-1.72 (4H, m), 3.09-3.00 (2H, m), 3.16 (2H, t, J=11.9 Hz), 3.46 (1H, t, J=6.1 Hz), 3.47 (2H, t, J=10.4 Hz), 3.73 (3H, s), 3.78 (2H, d, J=13.0 Hz), 10.4 (1H, s), 11.1 (1H, br s) ppm.

$^{13}$C-NMR (DMSO-d$_6$, TMS, 101 MHz): 22.7, 23.1, 29.6, 45.0, 45.4, 50.5, 50.6, 55.1, 55.2, 102.1, 105.2, 108.3, 109.2, 121.2, 124.0, 127.6, 129.5, 129.8, 142.7, 150.9, 160.2, 178.7 ppm.

Analysis for the formula C$_{25}$H$_{31}$N$_3$O$_6$ (469.54):

| Calculated: | C | 63.95 | H | 6.65 | N | 8.95%. |
|---|---|---|---|---|---|---|
| Found: | C | 63.80 | H | 6.81 | N | 8.81%. |

Example 10

3-{4-[4(7-Chloro-2,3-dihydrobenzo[1,4]dioxin-5-yl)piperazine-1-yl]-butyl}-5-fluoro-1,3-dihydro-2H-indol-2-one

The title compound is prepared according to process B by applying processing method 1 starting from 3-4-chlorobutyl) 3-ethyl-5-fluoro-1,3-dihydro-2H-indol-2-one and 1-(7-chloro-2,3-dihydrobenzo[1,4]dioxin-5-yl)-piperazine.

M.p.: 146-148° C. (hexane-ethyl acetate).

IR (KBr): 2946, 1720 (C=O), 752 cm$^{-1}$.

$^1$H-NMR (DMSO-d$_6$, TMS, 400 M): 1.34-1.17 (2H, m), 1.43-1.34 (2H, m), 1.99-1.78 (2H, m), 2.42 (4H, br s), 2.93 (4H, br s), 3.48 (1H, t, J=5.6 Hz), 4.23 (4H, s), 6.42 (1H, d, J=2.5 Hz), 6.56 (1H, d, J=2.4 Hz), 6.79 (1H, dd, J=4.5, 8.5 Hz), 6.99 (1H, dt, J=2.7, 9.1 Hz), 7.16 (1H, dd, J=1.8, 8.2 Hz), 10.34 (1H, s) ppm.

$^{13}$C-NMR (DMSO-d$_6$, TMS, 101 MHz): 23.1, 26.3, 29.5, 45.8 (d, J=1.9 Hz), 49.9, 52.8, 52.9, 57.7, 63.9, 64.1, 109.8 (d, J=8.0 Hz), 110.54, 110.6, 112.0 (d, J=24.4 Hz), 113.8 (d, J=22.9 Hz), 124.3, 131.8 (d, J=8.4 Hz), 135.1, 139.1 (d, J=1.9 Hz), 142.7, 144.4, 158.0 (d, J=235.7 Hz), 178.9 ppm.

Analysis for the formula C$_{24}$H$_{27}$ClFN$_3$O$_3$ (459.95):

| Calculated: | C | 62.67 | H | 5.92 | Cl | 7.71 | N | 9.14%. |
| Found: | C | 62.26 | H | 5.88 | Cl | 7.53 | N | 8.93%. |

Example 11

3-{4-[4-(5-Chloro-2-methoxyphenyl)-piperazine-1-yl]-butyl}-1,3-dihydro-2H-indol-2-one Monohydrochloride The title compound is prepared according to process B by applying processing method 2 starting from 3-(4-chlorobutyl)-3-ethyl-1,3-dihydro-2H-indol-2-one and 1-(5-chloro-2-methoxyphenyl)-piperazine.

M.p.: 91-94° C.

IR (KBr): 2583, 1708 (C=O) cm$^{-1}$.

$^1$H-NMR (DMSO-d$_6$, TMS, 400 MHz): 1.34-1.23 (2H, m), 1.92-1.70 (4H, m), 3.15-3.00 (6H, m), 3.59-3.40 (5H, m), 3.78 (3H, s), 6.84 (1H, d, J=7.7 Hz), 6.90 (1H, d, J=2.5 Hz), 6.95 (1H, dt, J=1.0, 7.4 Hz), 6.98 (1H, d, J=8.7 Hz), 7.04 (1H, dd, J=2.5, 8.7 Hz), 7.17 (1H, t, J=7.7 Hz), 7.27 (1H, d, J=7.2 Hz), 10.4 (1H, s), 11.06 (1H, br s) ppm.

$^{13}$C-NMR (DMSO-d$_6$, TMS, 101 MHz): 22.7, 23.1, 29.6, 45.0, 46.6, 50.9, 55.2, 55.9, 109.4, 113.4, 118.3, 121.4, 122.7, 124.2, 124.7, 127.8, 129.7, 140.8, 142.9, 150.8, 178.9 ppm.

Analysis for the formula C$_{23}$H$_{29}$Cl$_2$N$_3$O$_2$ (450.41):

| Calculated: | C | 61.33 | H | 6.49 | Cl | 15.74 | N | 9.33%. |
| Found: | C | 59.48 | H | 6.71 | Cl | 15.47 | N | 8.96%. |

Example 12

5-Fluoro-3-{4-[4-3-methoxyphenyl)-piperazine-1-yl]-butyl}-1,3-dihydro-2H-indol-2-one Monooxalate The title compound is prepared according to process B by applying processing method 3 starting from 3-(4-chlorobutyl)-3-ethyl-5-fluoro-1,3-dihydro2H-indol-2-one and 1-(3-methoxyphenyl)piperazine.

M.p.: 211-214° C.

IR (KBr): 3226, 1708 (C=O) cm$^{-1}$.

$^1$H-NMR (DMSO-d$_6$, TMS, 400 MHz): 1.28-1.15 (2H, m), 1.68-1.64 (2H, m), 1.94-1.76 (2H, m), 2.9 (2H, t, J=7.8 Hz), 3.18 (4H, s), 3.37 (4H, s), 3.49 (1H, t, J=5.6 Hz), 3.72 (3H, s), 6.43 (1H, d, J=8.0 Hz), 6.56 (1H, d, J=8.1 Hz), 6.51 (1H, s), 6.82 (1H, dd, J=4.4, 8.3 Hz), 7.20-7.12 (2H, m), 9.2-7.6 (2H, br s), 10.43 (1H, s) ppm.

$^{13}$C-NMR (DMSO-d$_6$, TMS, 101 MHz): 22.6, 23.6, 29.3, 45.6, 45.9, 50.9, 55.1, 55.5, 59.9, 102.2, 105.3, 108.5, 109.9 (d, J=8.0 Hz), 112.1 (d, J=24.4 Hz), 114.0 (d, J=23.3 Hz), 130.0, 131.6 (d, J=8.4 Hz), 139.2 (d, J=1.5 Hz), 151.3, 158.1 (d, J=235.7 Hz), 160.5, 164.5, 178.8 ppm.

Analysis for the formula C$_{25}$H$_{30}$FN$_3$O$_6$ (487.53):

| Calculated: | C | 61.59 | H | 6.20 | N | 8.62%. |
| Found: | C | 59.70 | H | 6.33 | N | 8.35%. |

What we claim is:

1. A 3-alkyl indol-2-one compound of the general Formula (I),

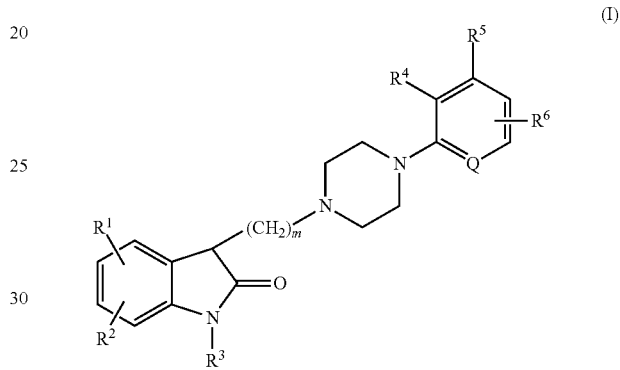

wherein

R$^1$ and R$^2$ independently represent hydrogen, halogen, alkyl or alkoxy having 1-7 carbon atom(s) or trifluoromethyl, R$^3$ is hydrogen, Q represents nitrogen, R$^4$ and R$^5$ independently represent hydrogen, and R$^6$ denotes hydrogen and m is 4; or Q is a CH group and R$^4$ and R$^5$ together form ethylenedioxy, and R$^6$ stands for halogen or alkoxy having 1 to 7 carbon atom(s), and m is 1, 2, 3, or 4; or Q is a CH group and R$^4$, R$^5$ and R$^6$ independently represent alkyl or alkoxy having 1 to 7 carbon atom(s) or halogen, and m is 1, 2, 3 or 4, or a pharmaceutically acceptable acid addition salt thereof.

2. 3-[4-(4-Pyridine-2-yl-piperazine-1-yl)-butyl]-1,3-dihydro-2H-indol-2-one, or a pharmaceutically acceptable acid addition salt thereof.

3. 3-{4-[4-(7-Chloro-2,3-dihydrobenzo[1,4]-dioxin-5-yl)-piperazine-1-yl]-butyl}-1,3-dihydro-2H-indol-2-one, or a pharmaceutically acceptable acid addition salt thereof.

4. 5-Fluoro-3-[4-(4-pyridin-2-yl-piperazine-1-yl)-butyl]-1,3-dihydro-2H-indol-2-one, or a pharmaceutically acceptable acid addition salt thereof.

5. 6-Fluoro-3-[4-(4-pyridin-2-yl-piperazine-1-yl)-butyl]-1,3-dihydro-2H-indol-2-one, or a pharmaceutically acceptable acid addition salt thereof.

6. 3-{4-[4-(3-Methoxyphenyl)-piperazine-1-yl]-butyl}-1,3-dihydro-2H-indol-2-one, or a pharmaceutically acceptable acid addition salt thereof.

7. 3-{4-[4-(7-Chloro-2,3-dihydrobenzo[1,4]-dioxin-5-yl)-piperazine-1-yl]-butyl}-5-fluoro-1,3-dihydro-2H-indol-2-one, or a pharmaceutically acceptable acid addition salt thereof.

8. 3-{4-[4-(5-Chloro-2-methoxyphenyl)-piperazine-1-yl]-butyl}-1,3-dihydro-2H-indol-2-one, or a pharmaceutically acceptable acid addition salt thereof.

9. 5-Fluoro-3-{4-[4-(3-methoxyphenyl)-piperazine-1-yl]-butyl}-1,3-dihydro-2H-indol-2-one, or a pharmaceutically acceptable acid addition salt thereof.

10. A pharmaceutical composition comprising as an active ingredient at least one of the compounds of the general Formula (I) according to claim 1 or a pharmaceutically acceptable acid addition salt thereof in admixture with one or more conventional carrier(s) or auxiliary agent(s).

11. A process for the preparation of the compounds of the general Formula (I) as defined in claim 1, which comprises (a) reacting a compound of the general Formula (II),

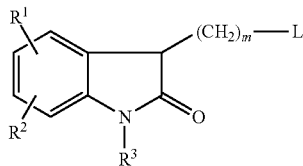

(II)

wherein L is hydroxy, with an arylsulfonyl chloride or a straight or branched chain alkylsulfonyl chloride having 1 to 7 carbon atom(s) and $R^1$, $R^2$, $R^3$, and m are as defined in claim 1 in the presence of an organic base, and reacting the thus-obtained compound of the general Formula (II), wherein L is arylsulfonyloxy or alkylsulfonyloxy, with a compound of the general Formula (III)

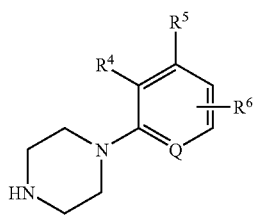

(III)

wherein Q, $R^4$, $R^5$, and $R^6$ are as defined in claim 1 in the presence of an acid binding agent, or (b) reacting a compound of the general Formula (V),

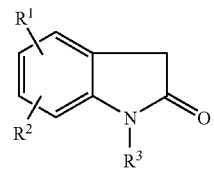

(V)

wherein $R^1$, $R^2$, $R^3$ are as defined in claim 1 with a compound of the general Formula (VI),

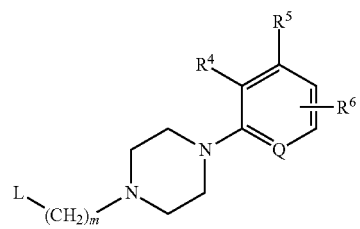

(VI)

wherein Q, $R^4$, $R^5$, $R^6$ are as defined in claim 1, m is 1, 2, 3 or 4, and L is a leaving group in the presence of a strong base.

12. A process for the manufacture of a pharmaceutical composition which comprises admixing at least one compound of the general Formula (I) according to claim 1 or a pharmaceutically acceptable acid addition salt thereof with a pharmaceutical carrier and optionally other auxiliary agent and bringing the mixture to galenic form.

13. A method for the treatment of generalized anxiety disorder, which comprises administering to a patient in need of such treatment a therapeutically effective amount of a pharmaceutical composition containing at least one compound of the general Formula (I) as defined in claim 1, or a pharmaceutically acceptable, organic or inorganic acid addition salt thereof.

14. The method of treatment according to claim 13, wherein said pharmaceutical composition is administered orally, parenterally, rectally, transdermally, or locally.

15. The method of treatment according to claim 13, wherein said pharmaceutical composition is administered in a daily dosage of 0.1-1000 mg/kg body weight.

16. The method of treatment according to claim 15, wherein said daily dosage is administered in one or more portion(s).

17. The pharmaceutical composition according to claim 9, wherein said active ingredient is present in an amount of 0.1-95% of the total composition.

18. The pharmaceutical composition according to claim 9, wherein said composition is in liquid, solid or soft form.

* * * * *